United States Patent [19]

Seitz et al.

[11] 3,983,115

[45] Sept. 28, 1976

[54] BIS-DIHALOGENO-S-TRIAZINYL UREAS

[75] Inventors: Karl Seitz, Oberwil; Rainer Begrich, Basel; Henri Riat, Arlesheim; Fritz Oesterlein, Basel, all of Switzerland

[73] Assignee: Ciba-Geigy Corporation, Ardsley, N.Y.

[22] Filed: Dec. 24, 1974

[21] Appl. No.: 536,131

[30] Foreign Application Priority Data
Jan. 9, 1974  Switzerland............................ 239/74

[52] U.S. Cl. .............................................. 260/249.5
[51] Int. Cl.² ........................................ C07D 251/44
[58] Field of Search ....................... 260/249.5, 249.6

[56] References Cited
UNITED STATES PATENTS
2,328,958  9/1943  D'Alelio et al. .................. 260/249.6
3,660,393  5/1972  Ackermann et al. ............... 260/249

Primary Examiner—John M. Ford
Attorney, Agent, or Firm—Joseph G. Kolodny; Edward McC. Roberts; Prabodh I. Almaula

[57] ABSTRACT

Bis-dihalogeno-s-triazinyl-ureas of the formula

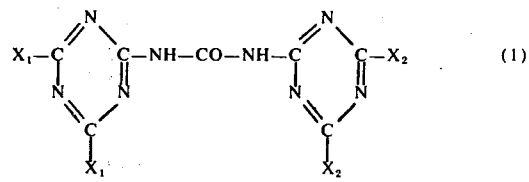

wherein each of $X_1$ and $X_2$ is halogen.

5 Claims, No Drawings

BIS-DIHALOGENO-S-TRIAZINYL UREAS

The present invention provides bis-dihalogeno-s-triazinyl-ureas of the formula

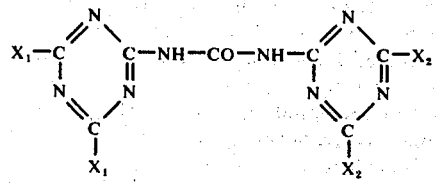   (1)

wherein each of $X_1$ and $X_2$ is halogen.

The substituents $X_1$ and $X_2$ can be the same or different. Fluorine, chlorine and bromine are suitable as substituents $X_1$, $X_2$. Preferably $X_1$ and $X_2$ are chlorine.

A preferred embodiment is the N,N'-bis-(4,6-dichloro-s-triazin-2yl)-urea of the formula

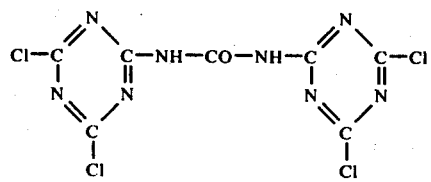   (2)

Bis-dihalogeno-s-triazinyl ureas of the formula (1) can be manufactured as follows:

a. Phosgene is reacted with 2-amino-4,6-diahlogeno-s-triazines of the formulae

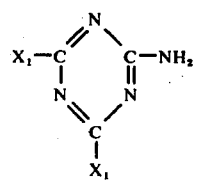   (3)

and

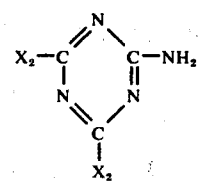   (4)

wherein $X_1$ and $X_2$ have the meaning assigned to them in the explanation of the formula (1).

The 2-amino-4,6-diahlogeno-s-triazines of the formulae (3) and (4) are obtained by condensation of 2,4,6-triahalogeno-s-triazines with ammonia.

N,N'-bis-(4,6-dichloro-s-triazin-2-yl)-urea of the formula (2) is obtained by process (a) by reacting phosgene with 2-amino-4,6-dichloro-s-triazine.

b. Bis-diahlogeno-s-triazinyl ureas of the formula

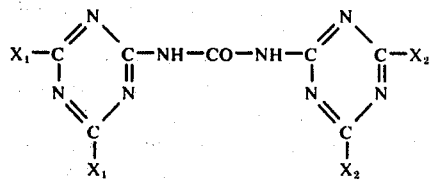   (5)

wherein each of $X_1$ and $X_2$ is halogen, can be manufactured by reacting 2-isocyanato-4,6-dihalogeno-s-triazines of the formula

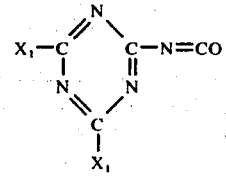   (6)

with 2-amino-4,6-dihalogeno-s-triazines of the formula

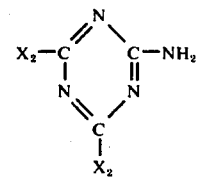   (7)

The 2-isocyanato-4,6-dihalogeno-s-triazines of the formula (6) can be obtained by reaction of 2-amino-4,6-dihalogeno-s-triazines with oxalic chloride (German Offenlegungsschrift 2 230 070).

N,N'-bis-(4,6-dichloro-s-triazin-2-yl)-urea of the formula (2) is obtained by process b) by reacting 2-isocyanato-4,6-dichloro-s-triazine of the formula

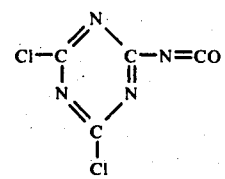   (8)

with 2-amino-4,6-dichloro-s-triazine of the formula

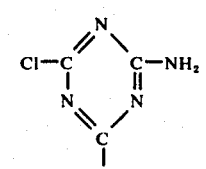   (9)

The compounds of the formulae (3) and (4) and (6) to (9) used as starting materials or intermediates in the manufacturing processes (a) and (b) are known and can be manufactured by known methods.

The acylations according to process (a) are desirably carried out using acid acceptors, for example sodium carbonate or sodium hydroxide, and under such conditions that, in the intermediates of the formulae (3) and (4) and (6) to (9) and in the end products of the formulae (1), (2) or (5), there still remain two halogen atoms in each s-triazine ring, i.e. in organic solvents or at relatively low temperatures in aqueous medium. To manufacture the N,N'-bis-(4,6-dichloro-s-triazin-2-yl)-urea by process (a), a solution of 2-amino-4,6-dichloro-s-triazine in acetone is reacted at 0° to 10°C with phosgene with the addition of 2 equivalents of an alkali hydrixide (referred to the total amount of 2-amino-4,6-dihalogeno-s-triazine) as a 10 normal aqueous alkaline solution.

The bis-dihalogeno-s-triazinyl-ureas of the formula (1) are characterised by high reactivity. They are particularly suitable as starting compounds for the manufacture of dyes, fluorescent brighteners, textile finishing agents or agrochemicals or as hardeners for gelatine.

By acylating, for example, a dye which contains a free amino group with a bis-dihalogeno-s-triazinyl urea of the formula (1), there is obtained a fibre-reactive dye of the formula

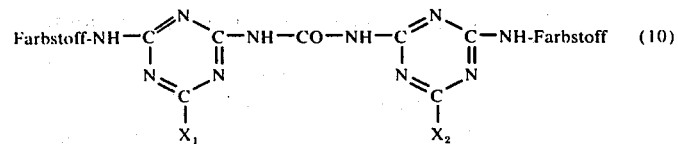

which is highly reactive in combination with cellulose fibres.

The following Examples illustrate the invention, the parts and percentages being by weight unless otherwise stated.

EXAMPLE 1

With cooling, 20 parts by volume of an aqueous 10 normal sodium hydroxide solution are added to a solution of 16.5 parts of 2-amino-4,6-dichloro-s-triazine in 250 parts of acetone. With good stirring, phosgene is bubbled in at 0°C until a sample diluted with water shows a pH of 5.5. Then a portion of the acetone (about 150 parts) is distilled off by rotary evaporation at as low a temperature as possible and the residue is drowned into 500 parts of ice water. The precipitate is filtered off, washed with water, dried and taken up in methylene chloride. A sparingly soluble byproduct is removed by filtration and the solvent is evaporated in vacuo to leave as residue N,N'-bis-(2,4-dichloro-s-triazin-2-yl)-urea in the form of a white powder. The product can be purified by dissolving it in hot chlorobenzene and precipitating it with ligroin.

Melting point: 214°C to 216°C (with decomposition) Analysis: $C_7H_2ON_8Cl_4 = 355.96$ estimated: C, 23.62; H, 0.57; N, 31.48; Cl, 39.84. found: C, 24.4; H, 0.8; N, 32.0; Cl, 39.2. The indicated structure was confirmed by the IR spectrum as well as by the mass spectrum.

The product contains two chlorine atoms in each triazine ring. One of those chlorine atoms in each ring can be easily replaced by the radical of metanilic acid at 10° to 40°C and pH 5. The content of pure substance can be ascertained exactly by this reaction (titration).

A solution of 3.56 parts of substance in 50 parts of acetone is added to 200 parts by volume of a 1/10 normal aqueous metanilic acid solution. The mixture is stirred for 1 hour at a temperature between 20° and 30°C and the pH is kept at 6 by neutralisation with normal sodium hydroxide solution. The surplus of metanilic acid is determined with sodium nitrite in the usual way. A content of pure substance of 98 to 99% follows therefrom.

EXAMPLE 2

4.12 parts of 2,4-dichloro-6-amino-s-triazine are dissolved in 70 parts by volume of acetonitrile. To this solution is added dropwise at room temperature a solution of 4.78 parts of 2,4-dichloro-6-isocyanato-s-triazine in 25 parts by volume of acetonitrile. The reaction mixture is refluxed for 4 hours and a clear solution is formed. After the reaction solution has cooled, the small amount of precipitate is filtered off with suction and the filtrate is evaporated to yield 7.41 parts of 1,3-bis-(2',4'-dichloro-s-triazine-6'-yl)-urea, which melts at 215°C after it has been purified by crystallisation.

Analysis: estimated: C, 23.6%; N, 31.4%; Cl, 39.8%. found: C, 23.2%; N, 31.4%; Cl, 40.0%.

EXAMPLE 3

[Structure of dye with SO₃H groups, azo linkage, NHCONH₂, and chloro-triazine bearing Cl]

[NH—CO] ₂

54.5 parts of the dye of the formula

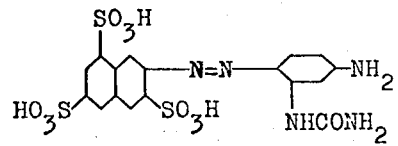

are dissolved in the form of the sodium salt in 500 parts of water and this solution is treated with a solution of 17.8 parts of N,N'-bis-(4,6-dichloro-s-triazin-2-yl)-urea in 100 parts of acetone. The mixture is stirred for 1 hour at room temperature and for about 2 hours at 40°C, the pH being kept between 5 and 6. When the condensation is terminated the resultant dye is precipitated by addition of acetone, filtered and dried. In the analysis, the dye contains one chlorine atom in each azo group. It dyes cotton in strong, golden yellow shades in the exhaustion process in the presence of alkali and electrolytes.

We claim:

1. Bis-dihalogeno-s-triazinyl-urea of the formula

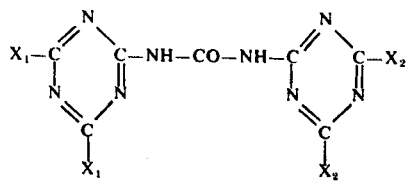  (1)

wherein each of $X_1$ and $X_2$ is halogen.

2. N,N'-bis-(4,6-dichloro-s-triazin-2-yl)-urea of the formula

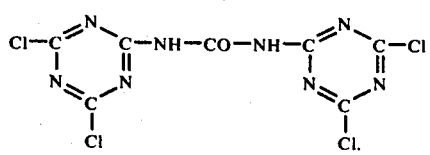  (2)

3. A process for the manufacture of bis-dihalogeno-s-triazinyl-ureas of the formula

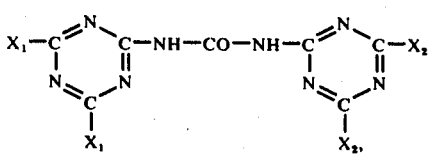  (1)

wherein each of $X_1$ and $X_2$ is halogen, which comprises reacting phosgene with 2-amino-4,6-dihalogeno-s-trizines of the formulae

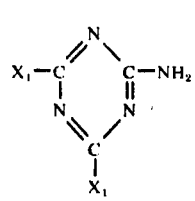  (3)

and (4)

4. A process according to claim 3 for the manufacture of N,N-bis-(4,6-dichloro-s-triazin-2-yl)-urea of the formula

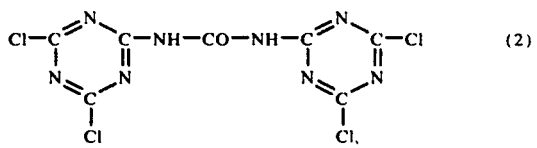  (2)

which comprises reacting phosgene with 2-amino-4,6-dichloro-s-triazine in the presence of an acid acceptor.

5. A process according to claim 4, which comprises carrying out the reaction in acetone with the addition of 2 equivalents of an aqueous alkali hydroxide (referred to the total amount of 2-amino-4,6-dihalogeno-s-triazines).

* * * * *